United States Patent
Beens et al.

(10) Patent No.: US 6,853,865 B2
(45) Date of Patent: Feb. 8, 2005

(54) APPARATUS FOR RF DIATHERMY TREATMENT

(75) Inventors: Jason A. Beens, San Antonio, TX (US); Stan K. Burton, San Antonio, TX (US); Daniel E. Nesthus, San Antonio, TX (US)

(73) Assignee: Selicor, Inc., Austin, TX (US)

( * ) Notice: Subject to any disclaimer, the term of this patent is extended or adjusted under 35 U.S.C. 154(b) by 0 days.

(21) Appl. No.: 10/234,989

(22) Filed: Sep. 4, 2002

(65) Prior Publication Data

US 2004/0044386 A1 Mar. 4, 2004

(51) Int. Cl.⁷ ................................................ A61F 2/00
(52) U.S. Cl. ...................... 607/103; 607/149; 607/154; 600/15
(58) Field of Search ................................ 607/101–103, 607/154, 149, 108, 111; 600/13–15, 388

(56) References Cited

U.S. PATENT DOCUMENTS

| | | | |
|---|---|---|---|
| 2,583,853 A | 1/1952 | Kazdin | 128/411 |
| 2,633,846 A | 4/1953 | Wray | 128/256 |
| 4,305,115 A | 12/1981 | Armitage | 361/437 |
| 4,368,410 A | 1/1983 | Hance et al. | 318/116 |
| 4,527,550 A | 7/1985 | Ruggera et al. | 128/1.5 |
| 4,685,462 A | 8/1987 | Olsen | 128/422 |
| 4,791,915 A | 12/1988 | Barsotti et al. | 128/24 |
| 4,873,995 A | 10/1989 | Kikuchi et al. | 128/804 |
| 5,160,828 A | 11/1992 | Olsen | 219/211 |
| 6,094,599 A | 7/2000 | Bingham et al. | 607/149 |

Primary Examiner—Roy D. Gibson
(74) Attorney, Agent, or Firm—Fulbright & Jaworski LLP

(57) ABSTRACT

Systems for RF diathermy treatment are described. An apparatus includes an RF diathermy coil assembly, comprising: an elastically deformable garment; and a conductive coil assembly secured to the garment, including: a primary winding; and a secondary winding coupled to the primary winding, the primary winding and the secondary winding being configured to optimize an impedance match between the conductive coil and an RF power source connected to the conductive coil.

23 Claims, 9 Drawing Sheets

APPARATUS FOR RF DIATHERMY TREATMENT

BACKGROUND OF THE INVENTION

1. Field of the Invention

The invention relates generally to the field of physical medicine treatment. More particularly, the invention relates to RF diathermy. Specifically, a preferred implementation of the invention relates to an RF diathermy coil assembly.

2. Discussion of the Related Art

Radio frequency (RF) coil systems can be used to provide heat to a patient's body, more specifically, to a limb or extremity. These systems are useful physical treatment instruments and serve as medical aids in several therapies, including: muscle healing, wound healing, and re-warming of hypothermia victims.

For example, U.S. Pat. No. 4,527,550 to Rugera et al. describes a coil designed for use under full wave operation at coil-wire length resonance. This system is limited to operation in an electromagnetic shielded room in order to meet FCC requirements. U.S. Pat. No. 5,160,828 to Olsen describes an apparatus for warming the extremities of a subject so that the subject can perform certain tasks in a cold environment. This apparatus can be operated in free-space, without shielding, while complying with environmental regulations.

A device and method for short-wave diathermy and/or neuromuscular simulation is described in U.S. Pat. No. 6,094,599 to Bingham et al., the disclosure of which is expressly incorporated herein by reference. The device can be used for treating slow or non-healing wounds due to vascular inefficiency, diabetic peripheral neuropathy, microangiography, microvascular disease, or compression neuropathies such as Carpal Tunnel Syndrome.

Heretofore, the requirements of providing a radio frequency coil system practicable for use in physical medicine treatment which has good electrical match characteristics, low power requirements, and that complies with environmental regulations have not been met. What is needed is a solution that addresses these requirements.

SUMMARY OF THE INVENTION

There is a need for the following embodiments. Of course, the invention is not limited to these embodiments.

According to an aspect of the invention, an apparatus includes an RF diathermy coil assembly, comprising: an elastically deformable garment; and a conductive coil assembly secured to the garment, including: a primary winding; and a secondary winding coupled to the primary winding, the primary winding and the secondary winding are configured to optimize an impedance match between the conductive coil and an RF power source connected to the conductive coil.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore nonlimiting, embodiments illustrated in the drawings, wherein like reference numerals (if they occur in more than one view) designate the same elements. The invention may be better understood by reference to one or more of these drawings in combination with the description presented herein. It should be noted that the features illustrated in the drawings are not necessarily drawn to scale.

DETAILED DESCRIPTION

The invention and the various features and advantageous details thereof are explained more fully with reference to the nonlimiting embodiments that are illustrated in the accompanying drawings and detailed in the following description. It should be understood that the detailed description, while indicating preferred embodiments of the invention, is given by way of illustration only and not by way of limitation. Various substitutions, modifications, additions and/or rearrangements within the spirit and/or scope of the underlying inventive concept will become apparent to one of ordinary skill in the art in light of this disclosure.

An RF diathermy coil assembly, representing an embodiment of the invention, can be cost effective and advantageous for at least the following reasons. The invention improves power transfer between the RF coil assembly system and a generator, thereby reducing the generator power output requirements for the same level of heating, and also facilitating compliance with environmental regulations by limiting the resonant portion of the system to the coil. The invention improves quality, promotes interoperability with other generators, and reduces costs compared to previous approaches.

Figure 1:
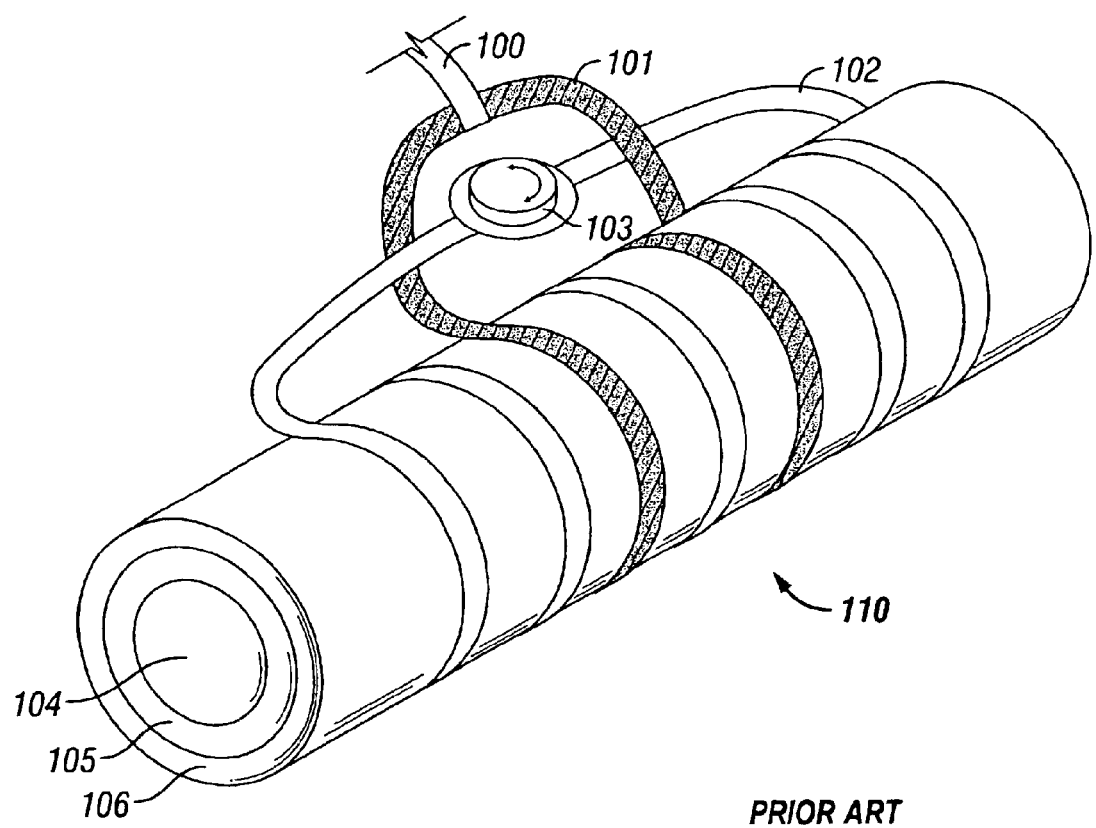
FIG. 1 is a functional block diagram of a prior art RF coil device.

Referring to FIG. 1, a functional block diagram of a prior art RF coil device 110 is depicted. The device includes a garment, which is made of a first and a second layer of fabric 105 and 106, respectively. Between the layers of fabric 105 and 106 there is a primary coil 101 and a secondary coil 102.

A patient's limb can be inserted into the garment via a tubular passage 104. A variable capacitor 103 is coupled to the secondary coil 102. A coaxial cable 100 is coupled to the primary coil 101, and the power is provided by an RF generator (not shown) through the coaxial cable 100. The ratio of windings between the secondary coil 102 and the primary coil 101 is 5:2, and the primary coil 101 is symmetrically located with respect to the windings of the secondary coil 102. The prior art RF coil device can be used for treating, for example, Carpal Tunnel Syndrome.

Figure 2A:
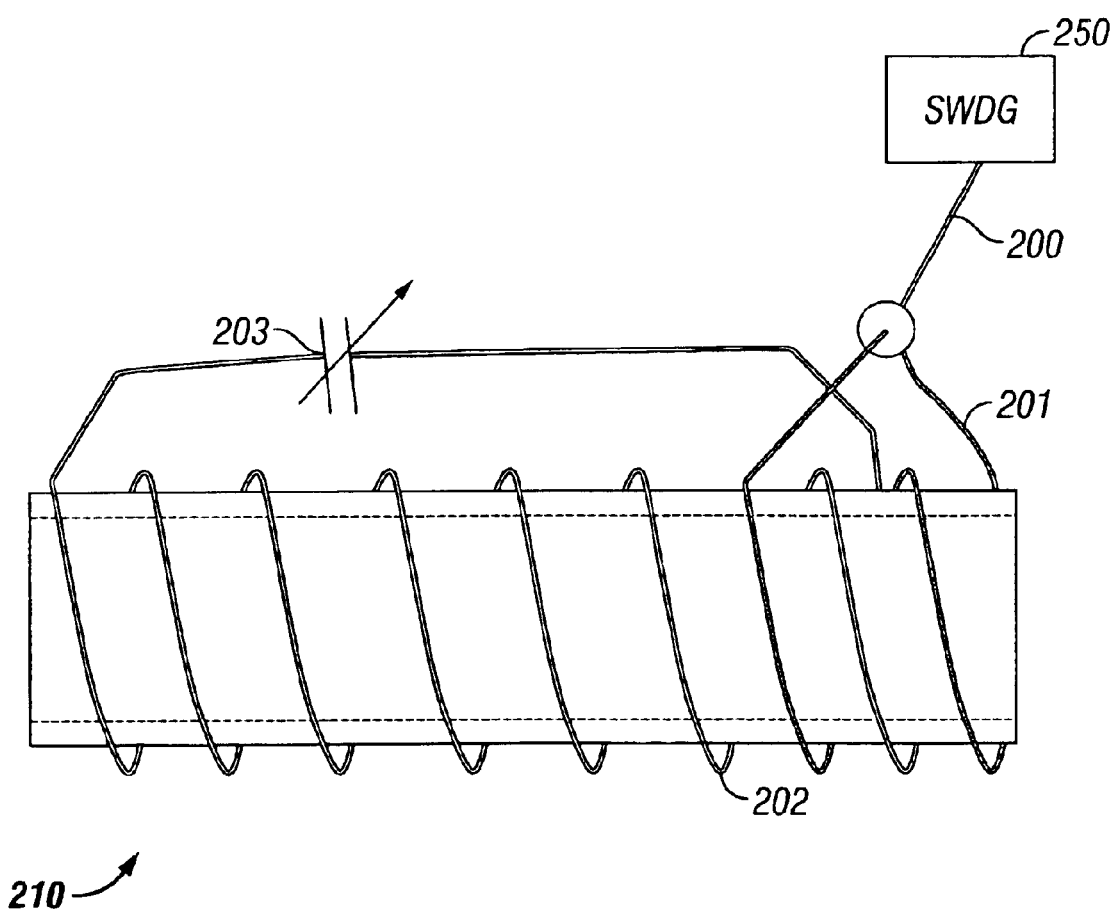
FIG. 2A is a schematic of an RF coil assembly, representing an embodiment of the invention.

Referring to FIG. 2A, a schematic of an RF coil assembly 210 in accordance with one embodiment of the present invention is depicted. A short-wave diathermy generator (RF power source) 250 is coupled to a garment cable 200. The garment cable 200 is coupled to a primary coil 201. The primary coil 201 is electro-magnetically coupled to a secondary coil 202, which includes a tuning capacitor 203. The primary coil 201 and secondary coil 202 are wrapped around a substantially cylindrical flexible garment 210. In the embodiment, the ratio of windings (turns ratio) between the primary coil 201 and the secondary coil 202 is 7:2, and the primary coil 201 is axially offset relative to the secondary coil 202. In the illustrated embodiment, one turn of the primary coil 201 is located outside of the secondary coil 202.

Figure 2B:
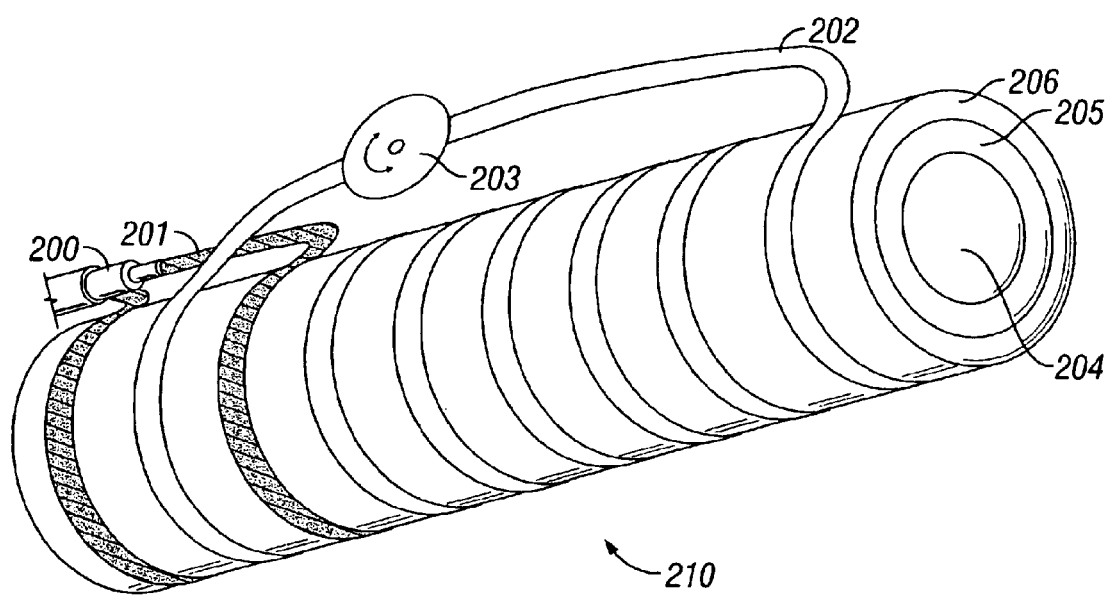
FIG. 2B is a functional block diagram of an RF coil assembly, representing an embodiment of the invention.

Referring to FIG. 2B, a functional block diagram of an RF coil assembly 210 in accordance with one embodiment of the present invention is depicted. The RF coil assembly 210 includes a flexible garment, which may be made of two layers 205 and 206. Between the layers 205 and 206 there is the primary coil 201 and the secondary coil 202. A limb may be inserted into the garment via the substantially deformable tubular passage 204. The tuning capacitor 203 is coupled to the secondary coil 202. The coaxial cable 200 is coupled to the primary coil 201, with power being provided by an RF generator (not shown). The ratio of windings between the primary coil 201 and the secondary coil 202 is 7:2, and the primary coil 201 is offset relative to the secondary coil 202, with one turn located outside of the secondary coil 202. The primary coil 201 and secondary coil 202 may be conductive coils, flexible conductive coils, woven wire conductive coils, or the like.

Figure 3:
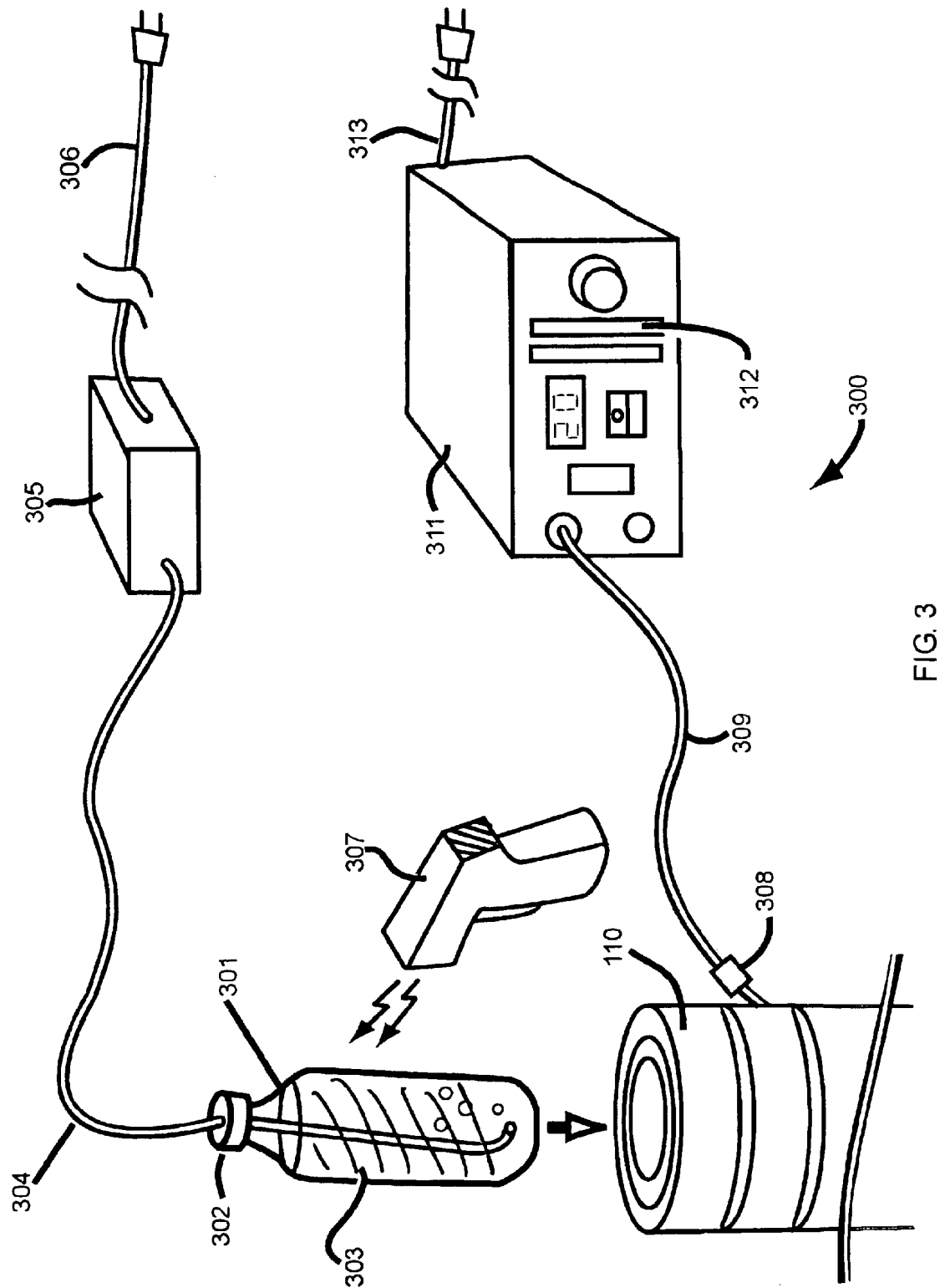
FIG. 3 is a diagram of test system used to illustrate aspects of the present invention.

Referring to FIG. 3, a diagram of a test system 300 used to illustrate aspects and advantages of the present invention is depicted. The test system 300 was devised to quantify the performance of any RF garment device, and is capable of measuring their electrical quality as well as their thermal delivery properties. A simulated human load 301 was constructed from a plastic bottle 302 filled with 710 ml of 0.9% NaCl saline solution diluted with distilled water 303. The bottle diameter measured 2¾ inches, or approximately the same as a medium-sized adult wrist. The bottle 302 was shaped so as to fit inside a garment under test. A non-conductive plastic tubing 304 was inserted in the cap of the bottle 302 and connected to an aerator device 305. The aerator 305 was connected to an AC power supply (not shown) via a power cord 306. The aerator 305 kept the saline solution 303 disturbed allowing for more uniform heating throughout the simulated human load 301, so that temperature measurements could be accurately taken by a handheld infrared thermometer 307.

Still referring to FIG. 3, a coaxial cable 309 approximately 3-feet long was connected to a Hewlett Packard HP 8753-D vector network analyzer (VNA) 311. The VNA 311 also serves as an RF generator. The VNA 311 was then calibrated with the coaxial cable 309 and an HP 85503D calibration kit (not shown), to eliminate the coaxial cable 309 from further measurements. As one of ordinary skill in the art will recognize, the length of a coaxial cable 309 can significantly affect the value measured with RF testing gear if the coil is not properly matched.

Referring to FIGS. 1 and 3, the prior art garment tested included a first layer of fabric 105 constructed from a foam former approximately ten inches in length, nine inches in circumference, and about ¼ inch in thickness. The second layer of fabric 106, typically a protective outer covering, was absent. The primary coil 101 and secondary coil 102 were both wound with 20 AWG insulated stranded copper wire and the ratio of secondary to primary turns was 5:2. The secondary coil 102 was centered axially relative to the primary coil, and wound onto the foam former with the wires spaced approximately 1 inch apart. Thus, the wire-to-wire spacing between the primary coil 101 and the secondary coil 102 was approximately ½ inch. The overall length of the secondary coil 102 was approximately 45 inches, or about ¹⁄₁₀ of a wavelength at an operating frequency of 27.12 MHz.

Still referring to FIGS. 1 and 3, a modification was made to the prior art RF coil device in order to accurately measure its electrical characteristics. The modification included fitting a BNC type RF connector 308 to the primary coil 101 where the coaxial cable 100 would normally connect. This allowed the effects of the coaxial cable 100 to be removed from the diathermy system, and allowed for direct measurement of the electrical performance of the coil assembly itself. The prior art RF coil device 110 was placed over the simulated load 301, and the BNC connector 308 was connected to the end of the calibrated coaxial cable 309. In this configuration, the VNA 311 can measure the electrical characteristics at the BNC connector 308. The VNA 311 was configured to measure a voltage standing wave ratio (VSWR) at and near the desired operating frequency of 27.12 MHz. The variable capacitor 103 was tuned to produce a minimum VSWR at 27.12 MHz. Further, the VNA 311 was used to generate a VSWR chart and also a complex impedance chart.

The test setup for the RF coil assembly 210 detailed in FIGS. 2A–2B in accordance with the present invention was identical to that of the prior art test detailed above. The secondary coil 202 was wound with a wire-to-wire spacing of approximately one inch. The secondary coil 202 consisted of seven turns of 20 AWG stranded insulated copper wire. The overall wire length was approximately 65 inches. The primary coil 201 was wound with the secondary coil 202 wires spaced about ½ inch apart. The turns ratio of the secondary to primary was 7:2 and the primary and secondary coils 201, 202 were axially off set relative to one another.

Referring to FIG. 3, in order to measure the warming delivery capability of the coils, the generator 311 was set to deliver full power, approximately 33 watts, and both the prior art coil and the RF coil assembly of the present invention were tuned for best match according to the display 312. The temperature of the saline solution 303 was measured and recorded at the beginning of the experiment with a handheld infrared thermometer 307, and again at the end of the experiment. A typical experiment lasted for about twenty minutes. The prior art RF coil device 110 produced a 9 degree Fahrenheit rise in saline temperature from 76° to 85° F. in twenty minutes. The present invention was able to create a temperature rise of 17 degrees Fahrenheit, warming the saline 203 from 77° to 94° F., also in twenty minutes. This experiment demonstrated an 89 percent improvement in thermal transfer capability for the present invention over the prior art. These temperature test results are illustrated in Table I (set forth below).

TABLE I

Temperature Test Results

| | Initial Temperature (° F.) | Final Temperature (° F.) |
|---|---|---|
| Prior art coil device | 76 | 85 |
| RF coil assembly of present invention | 77 | 94 |

Figure 4A:
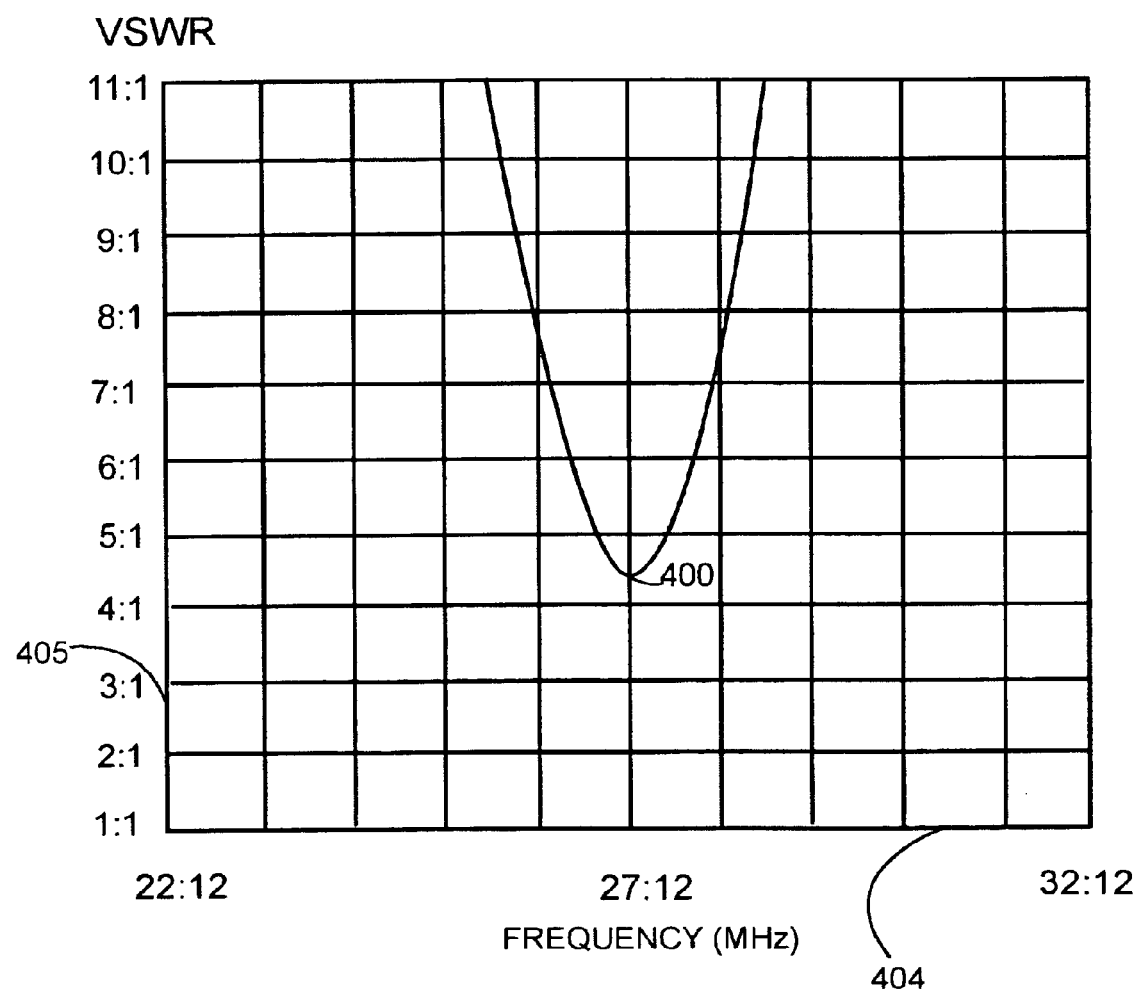
FIG. 4A is a voltage standing wave ratio graph characteristic of a prior art RF coil device.

Referring to FIG. 4A, a voltage standing wave ratio (VSWR) graph characteristic of a prior art RF coil device detailed in FIG. 1 is depicted. The graph shows a magnitude of a VSWR trajectory 400 of the match between the prior art coil device and the generator (VNA) 311 detailed in FIG. 3. The horizontal axis 404 shows the frequency of the measurement and has a scale of 1 MHz per division, extending from 22.12 MHz on the far left of the graph to 32.12 MHz on the far right of the graph. The center of the horizontal axis 404 is at 27.12 MHz, which is the desired frequency of operation for the prior art RF coil device. The vertical axis 405 indicates the VSWR and has a scaling of one unit per division, where the units are dimensionless ratios starting at the bottom of the graph with a ratio of 1:1. The top of the graph has a value of 11:1.

Still referring to FIG. 4A, an ideally matched garment would show a VSWR trajectory 400 that touches the 1:1 axis at least at the operating frequency of 27.12 MHz (the center of the horizontal axis). Any deviation from the 1:1 axis at the operating frequency of 27.12 MHz indicates an inefficiency in the RF match.

Figure 4B:
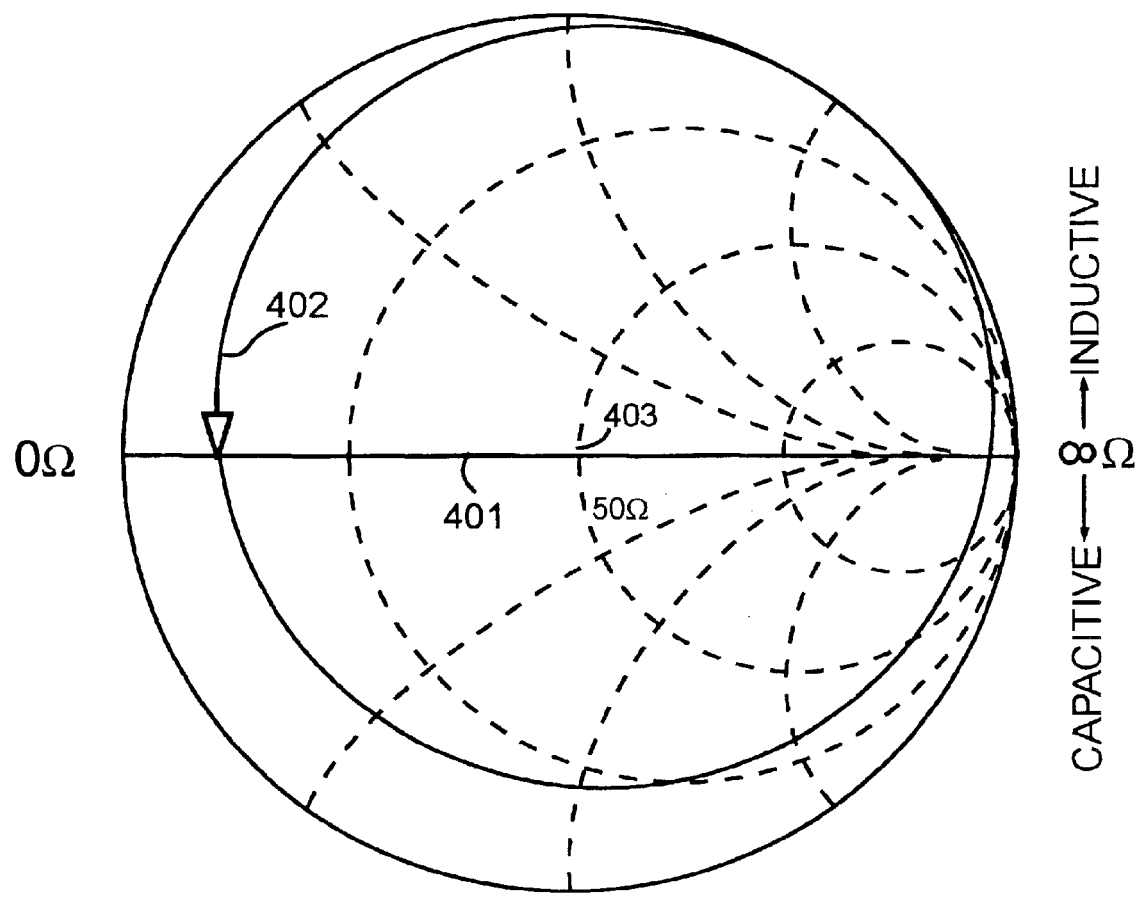
FIG. 4B is a complex impedance chart characteristic of a prior art RF coil device.

Referring to FIG. 4B, a complex impedance chart characteristic of the prior art RF coil device is depicted. This chart is known in the art as a Smith chart, showing a garment impedance trajectory 402 normalized to 50 ohms. The Smith chart also shows curves of constant resistance and constant reactance. The horizontal axis of the chart is referred to as a resistive axis 401, and it spans from 0Ω to ∞Ω. All points falling on the resistive axis 401 have neither inductance nor capacitance. The points on the resistive axis 401 near the far left of the chart represent very low resistances, while the points on the resistive axis 401 which lie on the far right of the chart represent very high resistances. The center point 403 of the resistive axis 401 indicates 50 ohms, which corresponds to the system impedance. The semi-circular area above the axis 401 represents an inductive area of operation, and the semi-circular area below the axis 401 represents a capacitive area of operation.

Still referring to FIG. 4B, in normal operation, the prior art RF coil device detailed in FIG. 1 is ideally tuned for resonance, which is neither capacitive nor resistive and should always produce a point somewhere on the resistive axis 401. The center of the chart 403 is the ideal operating point for the diathermy system, and the quality of electrical match between the prior art RF coil device 410 and a short-wave diathermy generator (SWDG) can be determined by how close to the chart's center 403 the impedance trajectory 402 passes.

Figure 5A:
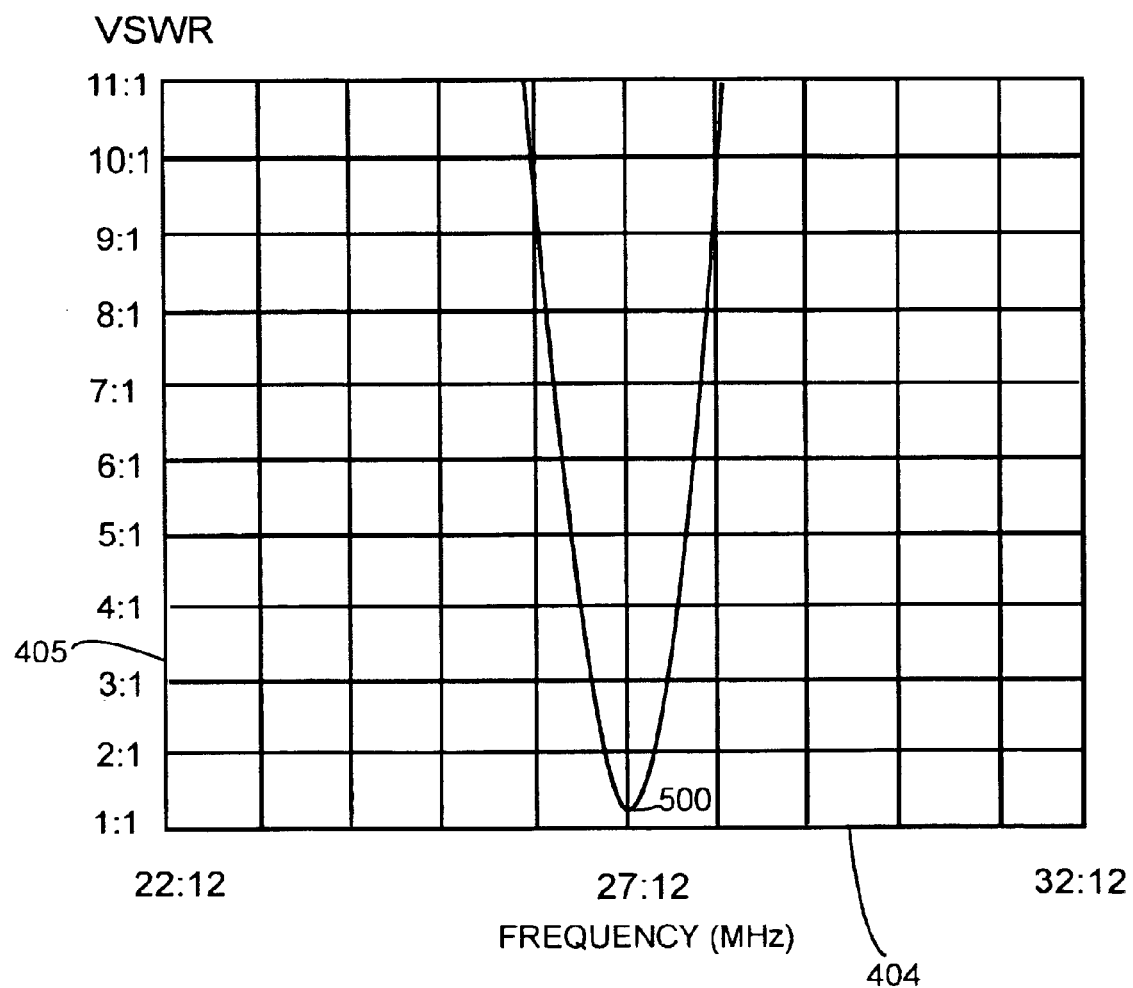
FIG. 5A is a voltage standing wave ratio graph characteristic of the RF coil assembly, representing an embodiment of the invention.

Referring to FIG. 5A, a voltage standing wave ratio (VSWR) graph characteristic of the RF coil assembly in accordance with one embodiment of the present invention is depicted, showing the magnitude 500 of the match between the RF coil assembly of the present invention and the SWDG 250 detailed in FIG. 2A. The horizontal axis 404 shows the frequency of the measurement. The horizontal axis 404 extends from 22.12 MHz on the far left of the graph to 32.12 MHz on the far right of the graph, with its center at 27.12 MHz. The vertical axis 405 indicates VSWR.

Figure 5B:
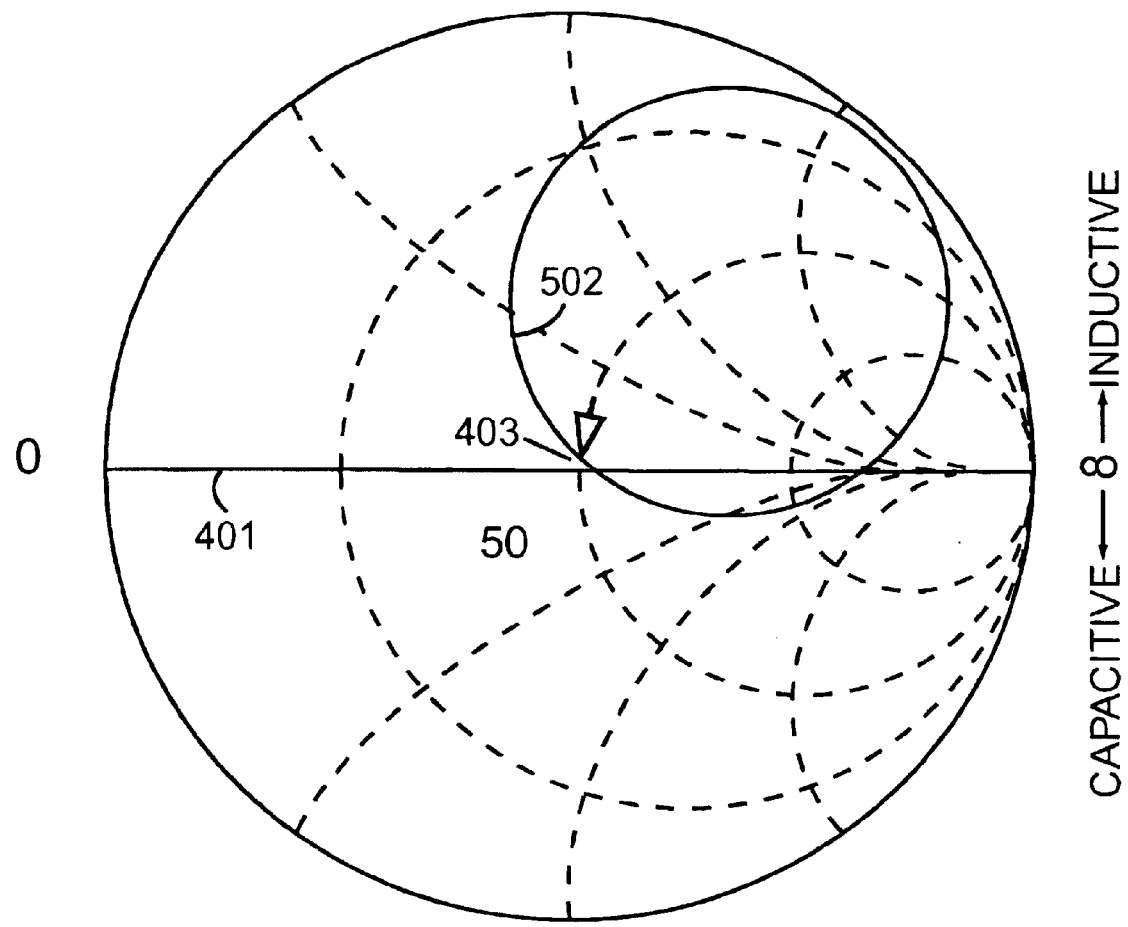
FIG. 5B is a complex impedance chart characteristic of the RF coil assembly, representing an embodiment of the invention.

Referring to FIG. 5B, a complex impedance chart characteristic of the RF coil assembly in accordance with one embodiment of the present invention is depicted. This Smith chart shows the impedance trajectory 502 normalized to 50 ohms. The horizontal axis 401 of the chart is the resistive axis, spanning from 0Ω to ∞Ω, with 50Ω at its center 403.

It can be seen from FIGS. 5A–5B, that by designing the RF coil assembly so that the ratio of secondary windings to primary windings is 7:2, the electrical match between the generator and garment is improved. Further, the effect of positioning the primary coil at an end of the secondary coil also improves the electrical match between the generator and the RF coil assembly. The RF coil assembly according to the present invention can achieve better impedance match with a 50-ohm system. FIGS. 5A–5B demonstrate substantially improved results compared to FIGS. 4A–4B, characteristic of the prior art. Specifically, the invention can provide an improvement in VSWR of at least a factor of 4.4.

The mechanisms which can affect the RF matching capabilities of the RF coil include: the ratio of secondary to primary turns, the overall size of the coils, and the non-uniform current and voltage distributions along the coil. The turns ratio has a transformer effect where the secondary and its impedance is reflected back to the primary by the square of the turns ratio. For example, a 7:2 coil is constructed to accept a SWDG with an output impedance near 50+j0 ohms. This equates to an impedance of $50* (7/2)^2=612.5$ ohms on the secondary coil. Thus, the area of the secondary coil located near the primary coil must produce an impedance of 612.5 ohms to match the primary coil output with that of the SWDG. By increasing or decreasing the turns ratio, different impedances can be reflected back to the primary coil.

The turns ratio also affects the voltage and currents in the system, as the relationship between voltage, current, and impedance is fixed. This gives the designer a measure of adjustment for impedance matching as well as maximum voltage and current control. For example, other coil configurations have been found to work with a turns ratio of 7:1, but these configurations produce very high voltages on the secondary of the coil because the primary voltage is reflected across the transformer by the turns ratio. These high voltages require attention to prevent dielectric heating, which can be a problem when insulating material is brought into the presence of a high voltage field. The overall size of the coil also affects the matching capabilities of the garment. In general, as the number of turns in the secondary increase, the inductance increases proportionally. A higher inductance secondary coil equates to a higher impedance coil, and produces the added benefit of requiring a smaller capacitance to tune the coil. The need for increasing the impedance of the coil is illustrated when FIG. 4B is compared to FIG. 5B. The prior art coil is low impedance, on the order of 12 ohms. This value is about four times lower than desired, and the coil must be adjusted to produce higher impedances. This was partially accomplished by adding two additional turns to the coil, and creating the 7:2 coil topology. The single parameter that affects the coil impedance at the primary coil output, is the primary coil offset. The offset of the primary coil determines what impedance on the secondary winding is transformed to the primary winding, and therefore to the SWDG. The movement of the primary coil with respect to the secondary coil allows the designer to choose, within the limitations of the coil, the impedance to reflect from the secondary to the primary.

The coils used in short-wave diathermy for human limbs are necessarily large with respect to the radio frequency wavelength at which they operate. For this reason, the secondary inductance of a coil cannot be treated as a lumped element, but must be thought of as a distributed system. In a resonant distributed system, there are regular minimums and maximums of RF voltage and RF current. An example of such a system would be a ½ wavelength dipole antenna. Such an antenna exhibits a high voltage and low current region at either end of the dipole. This forms a high impedance region. The center of the dipole exhibits a low voltage, high current region. This area is low impedance. As the impedance of the dipole is measured from center to either end, it can be shown that any impedance between the low impedance center and the high impedance end can be found, and used for matching purposes.

The coils described herein behave in the same manner. The area in the center of the coil is very low impedance, and therefore matching to the center of a coil may not be suitable for RF power transfer. The impedance of the area on the ends of the coil, nearest the tuning capacitor is high impedance and more easily matched to an RF generator. The current invention makes use of this property, as well as the increase in impedance afforded by the addition of the two secondary turns compared to the prior art.

Figure 6:
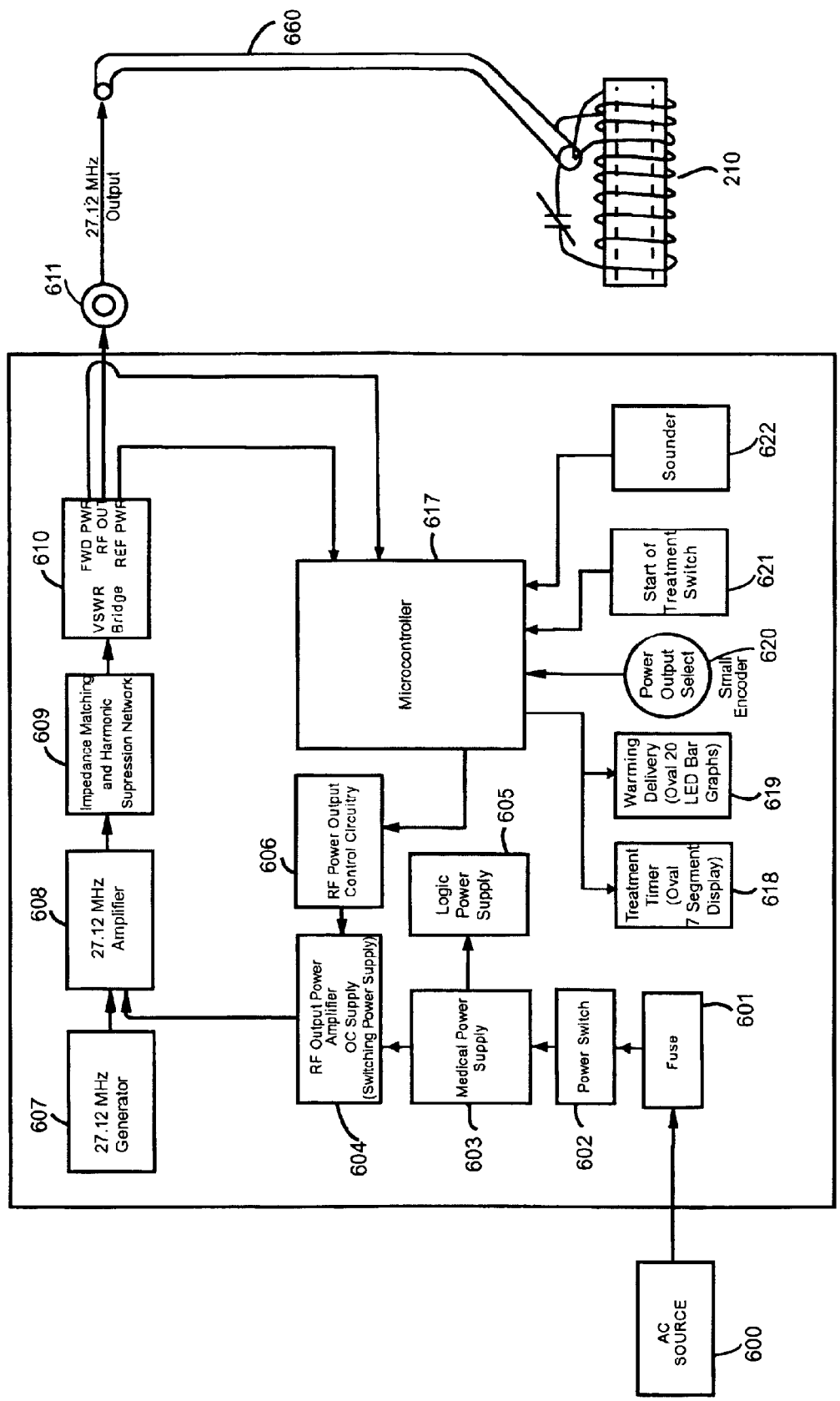
FIG. 6 is a block diagram of a short-wave diathermy generator (SWDG), representing an embodiment of the invention.

Referring to FIG. 6, a block diagram of a short-wave diathermy generator 650 is depicted. An AC source 600 is coupled to a power switch 602 via a fuse 601. The power switch 602 is coupled to a medical power supply 603. The medical power supply 603 is coupled to an RF output power amplifier DC supply 604 and to a logic power supply 605. The RF output power amplifier 604 can include a switching power supply and it is coupled to a 27.12 MHz amplifier 608 and to a microcontroller 617 via an RF power output control circuitry 606.

Still referring to FIG. 6, a 27.12 MHz generator 607 is coupled to a first impedance matching and harmonic suppression network 609 via the 27.12 MHz amplifier 608. The first impedance matching and harmonic suppression network 608 is coupled to a 27.12 MHz output 611 via a VSWR bridge 610. An RF diathermy garment assembly 660 including RF diathermy coil assembly 210 is coupled to the 27.12 MHz output connector 611. The VSWR bridge 610 is coupled to the microcontroller 617 via a forward power line and a reference power line. The microcontroller 617 is coupled to a treatment timer 618, a warming delivery 619, a power output selector 620, a start of treatment switch 621, and a sounder 622.

Still referring to FIG. 6, the short-wave diathermy generator is powered from an AC source 600, and is capable of producing RF power at 27.12 MHz (11.06 meters). In one embodiment, the short wave diathermy generator provides an indication of the RF power available and the RF power delivered. The generator can utilize the VSWR bridge 610 to measure the effects of the RF load on itself. The VSWR bridge 610 can be used to control the front panel display and RF protection circuitry built into the generator.

The invention can include an apparatus for RF diathermy treatment. The invention can also include an RF diathermy coil assembly.

The terms a or an, as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

All the disclosed embodiments of the invention disclosed herein can be made and used without undue experimentation in light of the disclosure. The invention is not limited by theoretical statements recited herein. Although the best mode of carrying out the invention contemplated by the inventors is disclosed, practice of the invention is not limited thereto.

The invention can also be included in a kit. The kit can include some, or all, of the components that compose the invention. The kit can also contain instructions for practicing the invention. Further, although the RF diathermy coil assembly described herein can be a separate module, it will be manifest that the RF diathermy coil assembly may be integrated into the system with which it is associated.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

What is claimed is:

1. An RE diathermy coil assembly, comprising:
    an elastically deformable garment; and
    a conductive coil assembly secured to the garment, including:
        a primary winding; and
        a secondary winding coupled to the primary winding, the primary winding being offset relative to the second winding to optimize an impedance match between the conductive coil and an RE power source connected to the conductive coil.

2. The RE diathermy coil assembly of claim 1, wherein a turns ratio of e secondary winding to the primary winding is approximately 7:2.

3. The RE diathermy coil assembly of claim 1, wherein one turn of the primary winding is located outside of the secondary winding.

4. The RE diathermy coil assembly of claim 1, wherein the garment includes a generally elastic deformable patient-conforming garment.

5. The RE diathermy coil assembly of claim 1, wherein the conductive coil includes a woven wire conductive coil.

6. The RE diathermy coil assembly of claim 5, wherein the conductive coil is operable to deform as the garment deforms.

7. The RE diathermy coil assembly of claim 1, wherein the secondary winding is electro-magnetically coupled to the primary winding.

8. The RE diathermy coil assembly of claim 1, wherein the primary winding is connectable to a power source lead.

9. The RE diathermy coil assembly of claim 1, further comprising a tuning circuit coupled to the conductive coil.

10. The RE diathermy coil assembly of claim 9, wherein the tuning circuit includes a balun.

11. The RE diathermy coil assembly of claim 9, wherein the tuning circuit includes a tuning capacitor.

12. The RE diathermy coil assembly of claim 1, further comprising an power source coupled to the primary winding.

13. An RE diathermy coil assembly, comprising:
    an elastically deformable garment; and
    a conductive coil secured to the elastically deformable garment, including:
        a primary winding; and
        a secondary winding coupled to the primary winding, wherein a turns ratio of the secondary winding to the primary winding is approximately 7:2.

14. The RE diathermy coil assembly of claim 13, wherein the primary winding is offset relative to the secondary winding.

15. The RE diathermy coil assembly of claim 13, wherein the garment includes a generally elastic deformable patient-conforming garment.

16. The RE diathermy coil assembly of claim 13, wherein the conductive coil includes a woven wire conductive coil.

17. The RF diathermy coil assembly of claim 16, wherein the conductive coil is operable to deform as the garment deforms.

18. The RE diathermy coil assembly of claim 13, wherein the second winding is electro-magnetically coupled to the primary winding.

19. The RE diathermy coil assembly of claim 13, wherein the primary winding is connectable to a power source lead.

20. The RF diathermy coil assembly of claim 13, further comprising tuning circuit coupled to the conductive coil.

21. The RE diathermy coil assembly of claim 20, wherein the tuning circuit includes a balun.

22. The RE diathermy coil assembly of claim 20, wherein the tuning circuit includes a tuning capacitor.

23. The RE diathermy coil assembly of claim 13, further comprising a short wave diathermy generator coupled to the primary winding.

* * * * *

UNITED STATES PATENT AND TRADEMARK OFFICE
CERTIFICATE OF CORRECTION

PATENT NO. : 6,853,865 B2
DATED : February 8, 2005
INVENTOR(S) : Beens et al.

It is certified that error appears in the above-identified patent and that said Letters Patent is hereby corrected as shown below:

Column 8,
Lines 22, 30, 32, 35, 38, 41, 46, 49, 51, 53, 55, 57 and 60, delete "RE" and insert -- RF -- therefor.
Line 29, delete "second" and insert -- secondary -- therefor.
Line 33, delete "of e" and insert -- of the -- therefor.
Line 58, delete "an power" and insert -- an RF power -- therefor.

Column 9,
Lines 1, 4, 7 and 12, delete "RE" and insert -- RF -- therefor.
Line 13, delete "second" and insert -- secondary -- therefor.

Column 10,
Lines 1, 5, 7 and 9, delete "RE" and insert -- RF -- therefor.

Signed and Sealed this

Twenty-sixth Day of July, 2005

JON W. DUDAS
*Director of the United States Patent and Trademark Office*